(12) United States Patent
Albright

(10) Patent No.: US 7,666,444 B2
(45) Date of Patent: Feb. 23, 2010

(54) ANTIPARASITIC COMPOSITION

(75) Inventor: Robert Bruce Albright, Chalfont, PA (US)

(73) Assignee: Wyeth, Madison, NJ (US)

( * ) Notice: Subject to any disclaimer, the term of this patent is extended or adjusted under 35 U.S.C. 154(b) by 1004 days.

(21) Appl. No.: 11/035,815

(22) Filed: Jan. 14, 2005

(65) Prior Publication Data

US 2005/0197302 A1    Sep. 8, 2005

Related U.S. Application Data

(60) Provisional application No. 60/541,162, filed on Feb. 2, 2004.

(51) Int. Cl.
*A01N 25/02* (2006.01)

(52) U.S. Cl. ..................... 424/405; 514/615

(58) Field of Classification Search .............. None
See application file for complete search history.

(56) References Cited

U.S. PATENT DOCUMENTS

| 4,005,218 | A | 1/1977 | Janssen et al. |
| 4,427,663 | A | 1/1984 | Mrozik |
| 5,169,846 | A | 12/1992 | Crooks |
| 6,340,672 | B1 * | 1/2002 | Mihalik ............... 514/30 |
| 6,492,340 | B2 | 12/2002 | Mihalik |
| 6,653,288 | B1 | 11/2003 | Beuvry et al. |
| 6,955,818 | B1 * | 10/2005 | Hacket et al. ............... 424/405 |
| 2002/0028780 | A1 | 3/2002 | Lukas et al. |

FOREIGN PATENT DOCUMENTS

| CN | 1375287 A | 10/2002 |
| WO | WO 94/28887 A1 | 12/1994 |
| WO | 95/05812 | 3/1995 |
| WO | 97/13508 | 4/1997 |
| WO | WO 97/13508 A1 | 4/1997 |
| WO | 02/09764 A1 | 2/2002 |
| WO | 03/066009 A1 | 8/2003 |
| WO | 03/072112 A1 | 9/2003 |
| WO | 03/072113 A1 | 9/2003 |
| WO | 03/099259 A1 | 12/2003 |
| WO | 2004/043445 A1 | 5/2004 |
| WO | 2004/047803 A1 | 10/2004 |
| WO | WO 2004/089239 A2 | 10/2004 |

\* cited by examiner

*Primary Examiner*—Neil Levy
(74) *Attorney, Agent, or Firm*—Gloria K. Szakiel; Barbara L. Renda

(57) ABSTRACT

There is provided an improved antiparasitic composition comprising an antiparasitically effective amount of an organic amine salt of closantel optionally a macrocyclic lactone and a non-irritating solvent system consisting essentially of an alcohol and a glycol derivative. Also provided are a method for obtaining increased levels of closantel in the blood of a homeothermic animal and a method for the enhanced protection of said animal from parasitic infection.

4 Claims, No Drawings

ANTIPARASITIC COMPOSITION

BACKGROUND OF THE INVENTION

Parasites, such as helminths, are found in many animals, particularly grazing animals, and are responsible for significant economic losses throughout the world. Among the helminths most frequently encountered in grazing animals such as cattle, horses, goats and sheep are trematodes, i.e., flukes, for instance, *Fasciola hepatica*, and nematodes such as *Haemonchus contortus*. A valuable tool for the treatment of homeothermic animals suffering from such parasites is closantel (U.S. Pat. No. 4,005,218 and Merck Index, 13$^{th}$ Edition).

Closantel is known to demonstrate little or no capacity for transdermal penetration at present, so the most effective means of administering closantel involves parenteral or oral administration. Commercially, Closantel is sold as its sodium salt, under Flukiver® for subcutaneous administration and Seponver® as an oral drench. Although the use of the sodium salt of closantel in a topical liquid composition is described in WO 97/13508, there still remains a need for closantel compositions which exhibit improved transdermal penetration properties, as well as increased bioavailability. It is apparent that, not withstanding high safety margins, a lower but effective dosage is always preferred.

Therefore, it is an object of this invention to provide improved antiparasitic compositions which, when administered to a homeothermic animal, increase the levels of closantel in the blood of said animal.

It is another object of this invention to provide a method for the enhanced protection of a homeothermic animal from parasitic infection.

It is a feature of this invention that the improved antiparasitic compositions may be administered to a homeothermic animal by topical, as well as parenteral, application, and whether alone, or in combination, with other antiparasitic compounds.

SUMMARY OF THE INVENTION

The present invention provides an antiparasitic composition having improved blood levels of closantel which comprises an antiparasitically effective amount of an organic amine salt of closantel, optionally an antiparasitically effective amount of a macrocyclic lactone, and a pharmacologically acceptable carrier.

Also provided is a method for the enhanced prevention, amelioration or control of a parasitic infection in a homeothermic animal which comprises administering to a homeothermic animal in need thereof a prophylactically, therapeutically or pharmaceutically effective amount of a composition comprising an organic amine salt of closantel, a pharmacologically acceptable carrier, and, optionally, a macrocyclic lactone.

DETAILED DESCRIPTION OF THE INVENTION

Although closantel is known to be effective as a flukicide, its topical application has been limited due to its low capacity for transdermal penetration. Surprisingly, it has now been found that an antiparasitic composition, having an organic amine salt of closantel as an active component, significantly increases the bioavailability of closantel. While not wishing to be bound by a particular theory, it is believed that in its organic amine salt form, such as an alkanol amine, for example, as the ethanolamine salt, closantel is absorbed by passive diffusion in the liver. This achieves higher liver levels and, consequently, higher blood levels. Hence, there is potential for increased antiparasitic activity against, for example, *Fasciola hepatica, Haemonchus contortus, Taenia pisiformis* or the like.

Advantageously, an antiparasitic composition of the invention containing an organic amine salt of closantel also demonstrates improved transdermal penetration properties, thus allowing for administration in the form of a pour-on composition. Pour-on compositions are particularly suitable for treating parasites in grazing animals such as cattle, goats or sheep. The composition of the invention is also suitable for administration by intramuscular or subcutaneous injection at a diversity of sites on an animal.

A further advantage of the use of the organic amine salt is that such can be more easily formulated with other anthelmintic agents, particularly those of the macrocyclic lactone type, which results in compositions that can be utilized to treat both nematodes and flukes (trematodes) in a single application.

Accordingly, the present invention provides an improved antiparasitic composition which comprises an antiparasitically effective amount of an organic amine salt of closantel, and a pharmacologically acceptable carrier, and optionally a macrocyclic lactone.

Organic amine salts of closantel suitable for use in the composition of the invention include alkanol amine salts such as ethanolamine, diethanolamine, methyl propanol amine, or the like; N-methyl glucamine, piperidine, piperazine, triethylamine, methyl amine, α-methylbenzyl amine, or the like. Highly preferred salts are the alkanol amine, and most preferred are the ethanolamine salts, i.e., closantel monoethanolamine or diethanolamine salts. Typically, such salts are prepared by contacting closantel with a solution of the organic amine. Organic amine salts are generally described, for instance, in U.S. Pat. No. 4,005,218.

Macrocyclic lactones suitable for use in the composition of the invention include milbemycins and avermectins such as moxidectin, abamectin, ivermectin, eprinomectin and doramectin or the like, and preferably moxidectin. These compounds, and their anthelmintic activity, are described more particularly in U.S. Pat. No. 4,916,154 (moxidectin), U.S. Pat. No. 4,310,519 (abamectin), U.S. Pat. No. 4,199,569 (ivermectin), U.S. Pat. No. 4,427,663 (eprinomectin), all of which are incorporated by reference.

The pharmacologically acceptable carrier for use in the compositions of the present invention can be selected from typical solvents and excipients utilized for veterinary formulations. Preferably, the organic amine salt of closantel is dissolved in the carrier, although suspensions in either liquid or gel formulations are also effective. When a macrocyclic lactone is included as an optional ingredient, it may be present either in solution or in suspension.

Alcohols suitable for use in the inventive composition include ethanol, benzyl alcohol, isopropanol, butanol, or a mixture thereof, with ethanol, benzyl alcohol or a mixture thereof being preferred.

Glycol derivatives suitable for use in the composition of the invention include propylene glycol, diethylene glycol monoethyl ether (transcutol), ethylene glycol, butylene glycol, polyethylene glycol, or the like, and preferably are propylene glycol, diethylene glycol monoethyl ether or a mixture thereof.

Antiparasitically effective amounts may vary according to the mode of application, the degree of infection, the target parasite species, the host homeothermic animal or the like. In general, amounts of about 5% w/v to 60% w/v of an organic amine salt of closantel, and optionally about 0.1% w/v to 5.0% w/v of a macrocyclic lactone, are suitable for use in the composition of the invention.

The compositions of the invention may also include excipients such as surfactants, preferably oleic acid, thickening agents, salts, buffers, polyvinylpyrrolidone, or any conventional inert excipient commonly used in a pharmaceutical composition. The amount of said excipients may range from about 0.1% w/v to about 20% w/v.

Typical compositions according to the invention may be prepared by admixing a glycol derivative with the organic amine salt of closantel and allowing said salt of closantel to solubilize to give a solution of the organic amine salt of closantel in the glycol derivative and treating this solution with an alcohol, which may optionally contain a macrocyclic lactone.

Advantageously, the compositions of the invention provide increased blood levels of closantel which are associated with the enhanced protection of a homeothermic animal against infection or infestation of parasites, particularly helminths.

Accordingly, the present invention provides a method for the enhanced prevention, amelioration or control of a parasitic infection in a homeothermic animal which comprises administering to a homeothermic animal in need thereof a prophylactically, therapeutically or pharmaceutically effective amount of an organic amine salt of closantel, optionally a macrocyclic lactone; and a pharmacologically acceptable carrier.

Homeothermic animals suitable for treatment in the method of the invention include grazing animals such as cattle, goats, sheep, llamas, deer, bison, etc.

The means of administration suitable for use in the inventive method include topical application and intramuscular or subcutaneous injection, with topical application being preferred.

Effective amounts may vary according to the general health of the animal, the degree of infection of infestation, the parasite species, the age of the animal, the organs infected or infested, or the like. In general, amounts of said composition sufficient to provide about 5 mg/kg to 100 mg/kg, preferably about 25 mg/kg to 50 mg/kg of closantel per body weight of the animal, and, optionally, about 0.1 mg/kg to 2.0 mg/kg, preferably about 0.1 mg/kg to 1.0 mg/kg of moxidectin per body weight of the animal are suitable.

For a clearer understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

In the following examples, the term "qs" designates "quantity sufficient."

EXAMPLE 1

Preparation of a Pour-On Formulation Containing an Organic Amine Salt of Closantel

| Ingredients | g/200 mL | % w/v |
|---|---|---|
| Closantel | 60.00 | 30.00 |
| Diethylene glycol | 60.0 | 30.00 |

-continued

| Ingredients | g/200 mL | % w/v |
|---|---|---|
| Monoethyl ether | | |
| Ethanol amine | 6.6 | 3.30 |
| Benzyl alcohol | 10.0 | 5.00 |
| Oleic acid | 60.0 | 30.00 |
| Moxidectin | 1.04 | 0.52 |
| Ethanol, USP | qs to 200 ml | qs to 100 |

A stirred mixture of closantel in diethylene glycol monoethyl ether is treated with ethanolamine, and stirring is continued until solution is complete, thus forming the salt in situ. To this solution is then added a solution of moxidectin in benzyl alcohol, followed by the addition of oleic acid and ethanol. Stirring is continued until the mixture is homogeneous.

EXAMPLE 2

Preparation of an Injectable Formulation Containing an Organic Amine Salt of Closantel

| | % w/v | |
|---|---|---|
| Ingredients | A | B |
| Ethanolamine salt of closantel | 12.9 | 16.0 |
| Glycerol formal | — | 40.0 |
| Propylene glycol | 45.0 | — |
| Benzyl alcohol | 10.0 | 10.0 |
| Polyvinylpyrrolidone | 7.0 | — |
| Deionized water | 7.0 | — |
| Ethanol, USP | 15.0 | — |
| Moxidectin (90%) | 1.1 | 2.0 |
| Polyethylene glycol | — | qs to 100 |
| Propylene glycol | qs to 100 | — |

Preparation of Injectable Formula A

To a solution of the ethanol amine salt of closantel in propylene glycol is added a solution of moxidectin in benzyl alcohol, with stirring until homogenous, thus forming the salt in situ. To this is then added a solution of polyvinylpyrrolidone in deionized water, ethanol and additional propylene glycol. The resultant mixture is stirred until homogeneous.

Preparation of Injectable Formula B

To a solution of the ethanol amine salt of closantel in glycerol formal is added a solution of moxidectin in benzyl alcohol, with stirring until homogenous. To this is then added polyethylene glycol and the resultant mixture is stirred until homogeneous.

EXAMPLES 3-5

Preparation of Ethanol Amine Closantel Pour-On Formulations Having 10% w/v, 20% w/v and 30% w/v Closantel Using essentially the same procedure described in Example 1, the pour-on formulations shown below are prepared.

EXAMPLE 3

10% w/v Closantel Pour-On

| Ingredient | % w/v |
|---|---|
| Closantel | 11.0 |
| Diethylene glycol Monoethyl ether | 30.0 |
| Ethanol amine | 1.3 |
| Oleic acid | 30.0 |
| 10% solution of Moxidectin in benzyl alcohol | 5.0 |
| Ethanol, USP | qs to 100 |

EXAMPLE 4

20% W/V Closantel Pour-On

| Ingredient | % w/v |
|---|---|
| Closantel | 22.0 |
| Diethylene glycol Monoethyl ether | 30.0 |
| Ethanol amine | 2.6 |
| Oleic acid | 30.0 |
| 10% solution of Moxidectin in benzyl alcohol | 5.0 |
| Ethanol | qs to 100 |

EXAMPLE 5

30% W/V Closantel Pour-On

| Ingredient | % w/v |
|---|---|
| Closantel | 33.0 |
| Diethylene glycol Monoethyl ether | 30.0 |
| Ethanolamine | 3.0 |
| Oleic acid | 19.0 |
| 10% solution of Moxidectin in benzyl alcohol | 15.0 |
| Ethanol | qs to 100 |

EXAMPLE 6

Preparation of a Pour-On Formulation Containing an Organic Amine Salt of Closantel

| Ingredients | g/200 mL | % w/v |
|---|---|---|
| Closantel | 66.00 | 30.00 |
| Diethylene glycol Monoethyl ether | 60.0 | 30.00 |
| Ethanolamine | 6.6 | 3.30 |
| Oleic acid | 60.0 | 30.00 |
| Ethanol, USP | qs to 200 ml | qs to 100 |

A stirred mixture of sodium closantel in diethylene glycol monoethyl ether is treated with ethanol amine, and stirring is continued until solution is complete, thus forming the salt in situ. To this solution is then added a solution of oleic acid and ethanol. Stirring is continued until the mixture is homogeneous.

EXAMPLE 7

Preparation of an Injectable Formulation Containing an Organic Amine Salt of Closantel

| Ingredients | % w/v A | % w/v B |
|---|---|---|
| Ethanol amine salt of closantel | 12.9 | 16.0 |
| Glycerol formal | — | 40.0 |
| Propylene glycol | 45.0 | — |
| Polyvinylpyrrolidone | 7.0 | — |
| Deionized water | 7.0 | — |
| Ethanol, USP | 15.0 | — |
| Polyethylene glycol | — | qs to 100 |
| Propylene glycol | qs to 100 | — |

Preparation of Injectable Formula A

A solution of the ethanolamine salt of closantel in propylene glycol is stirred until homogenous, thus forming the salt in situ. To this is then added a solution of polyvinylpyrrolidone in deionized water, ethanol and additional propylene glycol. The resultant mixture is stirred until homogeneous.

Preparation of Injectable Formula B

To a solution of the ethanolamine salt of closantel in glycerol formal is added polyethylene glycol and the resultant mixture is stirred until homogeneous.

EXAMPLES 8-10

Preparation of Ethanolamine Closantel Pour-On Formulations Having 10% w/v, 20% w/v and 30% w/v Closantel Using essentially the same procedure described in Example 6, the pour-on formulations shown below are prepared.

EXAMPLE 8

10% w/v Closantel Pour-On

| Ingredient | % w/v |
| --- | --- |
| Closantel | 11.0 |
| Diethylene glycol Monoethyl ether | 30.0 |
| Ethanolamine | 1.3 |
| Oleic acid | 30.0 |
| Ethanol, USP | qs to 100 |

EXAMPLE 9

20% w/v Closantel Pour-On

| Ingredient | % w/v |
| --- | --- |
| Sodium closantel | 22.0 |
| Diethylene glycol Monoethyl ether | 30.0 |
| Ethanol amine | 2.6 |
| Oleic acid | 30.0 |
| Ethanol | qs to 100 |

EXAMPLE 10

30% w/v Closantel Pour-On

| Ingredient | % w/v |
| --- | --- |
| Closantel | 33.0 |
| Diethylene glycol Monoethyl ether | 30.0 |
| Ethanolamine | 3.0 |
| Oleic acid | 19.0 |
| Ethanol | qs to 100 |

EXAMPLE 11

Pour on Formulation Containing the Aminomethylpropanol Salt of Closantel and Moxidectin

| Ingredient | % w/v |
| --- | --- |
| Closantel | 30.0 |
| Aminomethylpropanol | 2.2 |
| Diethylene glycol monoethyl ether | 30.1 |
| Moxidectin | 0.8 |
| Benzyl Alcohol | 7.3 |
| Oleic Acid | 30.0 |

Using the preparation scheme from Example 6, substitute aminomethylpropanol for ethanolamine.

EXAMPLE 12

Injectable Formulation Containing N-Methylglucamine Salt of Closantel and Moxidectin

| Ingredient | % w/v |
| --- | --- |
| N-methylglucamine Salt of Closantel | 18.75 |
| Moxidectin | 0.67 |
| Benzyl Alcohol | 10.00 |
| Ethanol | 15.00 |
| Propylene Glycol | q.s. |

N-methylglucamine is added to a suspension of closantel in ethanol, benzyl alcohol, and propylene glycol. With stirring, the salt of closantel forms in situ, forming a solution. Moxidectin is then added, and stirred until solution is obtained. The formulation is then brought to volume with propylene glycol.

EXAMPLE 13

Injectable Formulation Containing Diethanolamine Salt of Closantel and Moxidectin

| Ingredient | % w/v |
| --- | --- |
| Diethanolamine Salt of Closantel | 18.75 |
| Moxidectin | 0.67 |
| Benzyl Alcohol | 10.00 |
| Ethanol | 15.00 |
| Propylene Glycol | q.s. |

Diethanolamine is added to a suspension of closantel in ethanol, benzyl alcohol, and propylene glycol. With stirring, the salt of closantel forms in situ, forming a solution. Moxidectin is then added, and stirred until solution is obtained. The formulation is then brought to volume with propylene glycol.

Additional to the in situ formation of organic amine salts of closantel, these salts can be prepared, isolated and characterized by those skilled in the art.

EXAMPLE 14

A solution of closantel in a mixed solvent system of acetonitrile and tetrahydrofuran is treated with an equimolar amount of monoisopropanolamine. The reaction is stirred at 40° C., and then room temperature. Evaporation of the solvents leads to the isolation of the monoisopropanolamine salt of closantel. After purification using the standard methods, the salt is characterized.

EXAMPLE 15

A solution of closantel in a mixed solvent system of acetonitrile and tetrahydrofuran is treated with an equimolar amount of diisopropanolamine. The reaction is stirred at 40° C., and then room temperature. Evaporation of the solvents leads to the isolation of the diisopropanolamine salt of closantel. After purification using the standard methods, the salt is characterized.

Other additional excipient solvents can be used, such as N-methylpyrrolidone, 2-pyrrolidone or other pharmaceutically acceptable pyrrolidone solvents such as other alkyl or substituted alkyl pyrrolidones.

EXAMPLE 16

Injectable Formulation Containing Ethanolamine Salt of Closantel and Moxidectin

| Ingredient | % w/v |
|---|---|
| Monoethanolamine Salt of Closantel | 12.6 |
| Moxidectin | 1.0 |
| Benzyl Alcohol | 10.0 |
| 2-pyrrolidone | 38.3 |
| Polyethylene Glycol 400 | q.s. |

Ethanolamine is added to a suspension of closantel in benzyl alcohol, 2-pyrrolidone and polypropylene glycol 400. With stirring, the salt of formed in situ, forming a solution. Moxidectin is then added, and stirred until solution is obtained. The formulation is then brought to volume with PEG 400.

Solvents for the formation of acceptable pour on and/or injectable formulations of the alkanolamine salts of closantel are not limited to the aforementioned examples. Solvents which are pharmaceutically acceptable for dermal application can be used. Examples include, but are not limited to: 2-pyrrolidone, N-methylpyrrolidone, Polyethylene glycol 200, Polyethylene glycol 400 and other PEG molecular weight cuts, other alkyl pyrrolidones such as lauryl pyrrolidone, octyl pyrrolidone, and hydroxyethyl pyrrolidone, gamma-hydroxylactone, benzyl alcohol, dimethyl isosorbide, gycerol formal, dimethylacetamide, aromatic petroleum solvents, PPG2 myristyl ether propionate, other alkyl ether alkyl esters, mixed capric/caprylic glyceryl triesters and other mixed esters of glycerol.

EXAMPLE 17

Pour on Formulation Containing the Aminomethylpropanol Salt of Closantel and Moxidectin

| Ingredient | % w/v |
|---|---|
| Closantel | 30.0 |
| Aminomethylpropanol | 2.2 |
| Diethylene glycol monoethyl ether | 30.1 |
| Moxidectin | 0.8 |
| Benzyl Alcohol | 7.3 |
| Oleic Acid | 30.0 |

Using the preparation scheme from Example 6, substitute aminomethylpropanol for ethanolamine.

EXAMPLE 18

Comparative Evaluation of the Blood Levels of Closantel Following the Application of a Pour-On Formulation Containing the Sodium Salt of Closantel Vs the Ethanolamine Salt of Closantel In this evaluation weaned Holstein steer calves are treated with fenbendazole to remove any nematode infections present. The calves are then divided into test groups and maintained in accordance with the guidelines in the current Guide for the Care and Use of Agricultural Animals in Agricultural Research and Teaching. Animals are blocked into three blocks based on body weight and each animal within a block is randomly assigned to treatment group A or B. On day 0 of the study, all animals are weighed and each animal in each group is treated with a pour-on formulation as indicated in the experimental design. The pour-on formulations are administered at a rate of 0.1 mL formulation per kg of body weight (rounded to the nearest full mL). The test pour-on formulations are applied directly to the hair and skin in a narrow strip extending along the top of the back from the withers to the base of the tail. Application is made to the healthy skin, avoiding any scabs, skin lesions or extraneous foreign matter. Treatment is made using unarmed disposable syringes. The correct dose volume is calculated based on each animal's body weight on the day of treatment.

On Day 0, prior to treatment, and on Day 1, 2, 3, 4, 7, 10, 14, 21 and 28 post treatment, blood samples are collected from each experimental animal. The blood samples are centrifuged soon after collection at about 1000×g for approximately 25 minutes. Plasma is removed and equal amounts are stored at −20° C. During handling and storage, care is taken not to expose the plasma samples to direct sunlight. Duplicate plasma samples from each animal are analyzed for closantel. The results are shown in Table I.

Treatment A

Sodium Closantel Pour-On

| Ingredient | g/200 mL | % w/v |
|---|---|---|
| sodium closantel | 66.0 | 33.0 |
| propylene glycol | 60.0 | 30.0 |
| diethylene glycol monoethyl ether | 60.0 | 30.0 |
| benzyl alcohol | 10.0 | 5.0 |
| moxidectin | 1.0 | 0.5 |
| ethanol | qs to 200 mL | qs to 100 |

Using essentially the same procedure described in Example 1 and employing the ingredients listed hereinabove, a sodium closantel pour-on was prepared and used in this evaluation as treatment A.

Treatment B

Ethanolamine Closantel Pour-On

The ethanolamine closantel pour-on formulation described in Example 1 was used in this evaluation as treatment B.

Summary of Results

As can be seen from the data shown on Table I the composition of the invention demonstrates a significant increase in the blood levels of closantel alkanol amine salts.

TABLE I

| Treatment Group | Dose mg/kg | | μg closantel/mL plasma | | | | | | | |
|---|---|---|---|---|---|---|---|---|---|---|
| | | | Day 2 | Day 3 | Day 4 | Day 7 | Day 10 | Day 14 | Day 21 | Day 28 |
| A | 30 | | 5.47 | 5.98 | 6.35 | 7.3 | 9.35 | 10.5 | 8.70 | 8.30 |
| A | 30 | | 4.32 | 5.07 | 5.64 | 6.84 | 5.93 | 5.94 | 4.56 | 2.97 |
| A | 30 | | 8.39 | 10.39 | 11.39 | 12.55 | 13.95 | 15.11 | 10.21 | 8.98 |
| | | Avg. | 6.06 | 7.15 | 7.8 | 8.90 | 9.74 | 10.52 | 7.80 | 6.80 |
| B | 30 | | 7.22 | 10.61 | 11.73 | 14.66 | 15.68 | 15.51 | 16.77 | 14.23 |
| B | 30 | | 3.9 | 6.21 | 7.66 | 9.97 | 11.65 | 14.44 | 13.58 | 14.38 |
| B | 30 | | 6.7 | 12.97 | 17.46 | 18.89 | 20.52 | 28.53 | 25.09 | 19.08 |
| | | Avg. | 5.94 | 9.93 | 12.28 | 14.51 | 15.95 | 19.49 | 18.48 | 15.90 |

What is claimed is:

1. An antiparasitic composition which comprises:
an ethanolamine salt of closantel in an amount of about 5% w/v to 60% w/v;
moxidectin in an amount of about 0.1% w/v to 5% w/v; and
a pharmaceutically acceptable carrier.

2. The composition according to claim 1 wherein the pharmacologically acceptable carrier comprises benzyl alcohol, ethanol or a mixture thereof.

3. The composition according to claim 1 wherein the pharmacologically acceptable carrier comprises propylene glycol, diethylene glycol monoethyl ether or a mixture thereof.

4. The composition according to claim 1 wherein the ethanolamine salt of closantel is present at about 10% w/v to 35% w/v and the moxidectin is present at about 0.5% w/v to 2.0% w/v.

* * * * *

UNITED STATES PATENT AND TRADEMARK OFFICE
CERTIFICATE OF CORRECTION

PATENT NO. : 7,666,444 B2 Page 1 of 1
APPLICATION NO. : 11/035815
DATED : February 23, 2010
INVENTOR(S) : Robert Bruce Albright It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1358 days.

Signed and Sealed this

Seventh Day of December, 2010

David J. Kappos
*Director of the United States Patent and Trademark Office*